(12) United States Patent
Yanagibayashi et al.

(10) Patent No.: US 10,384,174 B2
(45) Date of Patent: Aug. 20, 2019

(54) PARTICLE OPERATION METHOD AND PARTICLE OPERATION DEVICE

(71) Applicants: SHIMADZU CORPORATION, Nakagyo-Ku, Kyoto-Shi, Kyoto (JP); KAZUSA DNA RESEARCH INSTITUTE, Kisarazu-Shi, Chiba (JP)

(72) Inventors: Jun Yanagibayashi, Kyoto (JP); Tetsuo Ohashi, Kyoto (JP); Osamu Ohara, Kisarazu (JP)

(73) Assignees: SHIMADZU CORPORATION, Kyoto (JP); KAZUSA DNA RESEARCH INSTITUTE, Chiba (JP)

( * ) Notice: Subject to any disclaimer, the term of this patent is extended or adjusted under 35 U.S.C. 154(b) by 187 days.

(21) Appl. No.: 15/526,374

(22) PCT Filed: Nov. 17, 2014

(86) PCT No.: PCT/JP2014/080317
§ 371 (c)(1),
(2) Date: May 12, 2017

(87) PCT Pub. No.: WO2016/079779
PCT Pub. Date: May 26, 2016

(65) Prior Publication Data
US 2017/0326509 A1 Nov. 16, 2017

(51) Int. Cl.
*B01F 3/12* (2006.01)
*B01J 8/20* (2006.01)
*B01F 9/02* (2006.01)
*B01J 19/08* (2006.01)
*B03C 1/00* (2006.01)
(Continued)

(52) U.S. Cl.
CPC ............ *B01F 3/12* (2013.01); *B01F 9/02* (2013.01); *B01F 9/10* (2013.01); *B01F 11/0082* (2013.01); *B01F 13/0809* (2013.01); *B01J 8/20* (2013.01); *B01J 19/08* (2013.01); *B03C 1/00* (2013.01); *B03C 1/01* (2013.01); *B03C 1/0332* (2013.01); *B03C 1/0335* (2013.01); *B03C 1/288* (2013.01); *C12M 1/42* (2013.01); *B03C 2201/18* (2013.01); *B03C 2201/26* (2013.01)

(58) Field of Classification Search
None
See application file for complete search history.

(56) References Cited

FOREIGN PATENT DOCUMENTS

JP 09-154833 6/1997
JP 2011-180111 9/2011
(Continued)

OTHER PUBLICATIONS

PCT/JP2014/080317, International Search Report dated Feb. 24, 2015, 2 pages—Japanese, 2 pages—English.

*Primary Examiner* — Changhwa J Cheu
(74) *Attorney, Agent, or Firm* — Andrew F. Young, Esq.; Lackenbach Siegel, LLP (57) ABSTRACT

The present invention relates to a particle manipulation method to disperse magnetic particles 70 in a liquid 35 filling up a tube container 10, wherein a circumferential direction moving step to move the magnetic particles 70 along the circumferential direction of the container 10 in the liquid 35 and in a radial direction moving step to move the magnetic particles 70 as crossing the radial direction of the container 10 in the liquid 35 are implemented repeatedly. Such manipulations can be achieved by combining rotation of the container and gravity force and magnetic field manipulations.

11 Claims, 5 Drawing Sheets

(51) Int. Cl.
*B01F 9/10* (2006.01)
*B03C 1/01* (2006.01)
*B03C 1/033* (2006.01)
*B03C 1/28* (2006.01)
*C12M 1/42* (2006.01)
*B01F 11/00* (2006.01)
*B01F 13/08* (2006.01)

(56) References Cited

FOREIGN PATENT DOCUMENTS

| | | |
|---|---|---|
| JP | 2012-239996 | 12/2012 |
| WO | WO 97/044671 | 11/1997 |
| WO | WO 2012/086234 | 6/2012 |
| WO | WO 2014/057907 | 4/2014 |

PARTICLE OPERATION METHOD AND PARTICLE OPERATION DEVICE

CROSS REFERENCE TO RELATED APPLICATIONS

This application relates to, and claim priority from Ser. No.: PCT/JP2014/080317 filed Nov. 17, 2014, the entire contents of which are incorporated herein by reference.

FIGURE SELECTED FOR PUBLICATION

FIG. 1

BACKGROUND OF THE INVENTION

Field of the Invention

The present invention relates to a manipulation method of a particle to perform chemical processes including a separation, an extraction, a purification and a chemical reaction and so forth of a target substance and further relates to a device for a particle manipulation applied thereto.

Description of the Related Art

Relative to a medical examination, food safety and hygienic control and monitoring of environment reservation and so forth, a target substance to be detected or subject to a chemical reaction must be extracted from the sample containing a variety of foreign (unwanted) materials. For example, such medical examination may have to perform detection, identification and quantification of nucleic acids, proteins, saccharides, lipids, bacteria, viruses and radioactive substances and so forth included in e.g., blood, serum, cells, urine and feces and so forth separated and obtained from plants and animals. In such examination, separation and purification of the target substance may be needed to eliminate a maleffect relative to the background and so forth due to foreign materials.

A method of separation and purification of the target substance in the sample using magnetic particles having a particle diameter in the range of approximately 0.5 μm to ten-odd-μm, of which surface functions as chemical affinity for and molecular recognition of the target substance, has been developed and commercialized. According to the above method, the process, in which the magnetic particles are separated and recovered from the liquid layer by the magnetic field manipulation following fixation of the target substances to the surface of the magnetic particles followed by, if needed, dispersing the recovered magnetic particles into the liquid layer such as a washing solution and separating-recovering the magnetic particles from the liquid layer, is repeated. Subsequently, the magnetic particles are dispersed in the eluate, so that the target substance fixed to the magnetic particles can be freed, and consequently, the target substance in the eluate can be recovered. The target substance is able to be recovered because of applying the magnetic particles, so that the above process can be advantageous to an automation for chemical extraction and purification.

The magnetic particles capable of selectively fixing the target substance is commercially available as a part of a separation-and-purification kit. Such kit includes a plurality of chemical agents in an individual vial (container) and the user pipettes such chemical agents for use. In addition, a device to automate such pipetting manipulation and magnetic field manipulation is also commercially available (Patent Document 1). On the other hand, instead of pipetting manipulation, the method using the device that is a capillary tube layered alternatively with liquid layer of dissolution and fixation solution, washing solution, eluate and so forth and a gelled medium layer is proposed, in which the magnetic particles are moved inside such device in the longitudinal direction of the tube to separate-and-purify the target substance (Patent Document 2). In addition, it is proposed that antigen-antibody reaction of the substance fixed on the surface of the magnetic particles inside liquid layer is performed and a measurement, such as an ELISA (enzyme-linked immunosorbent assay), is carried out using the tube device in which the liquid layer and the gelled medium layer are layered alternately (Patent Document 3).

RELATED PRIOR ART DOCUMENTS

Patent Document

Patent Document 1: WO1997/044671 A
Patent Document 2: WO2012/086243 A
Patent Document 3: WO2014/057907 A*

ASPECTS AND SUMMARY OF THE INVENTION

Objects to be Solved

Relative to the chemical operation using the magnetic particles, particles have to be dispersed in the liquid and the particle surface and the liquid must satisfactorily contact to each other in each stage including fixation of the target substance on the particle surface, washing-out of the foreign materials, reaction of the target substance fixed on the particle surface, elution of the target substance and so forth. When dispersed in the liquid, the operation must be performed while dissolving (uncoupling) the aggregate of the magnetic particles because the magnetic particles aggregate due to the magnetic field manipulation.

Relative to a liquid flow by a pipetting manipulation, dispersion of the aggregated magnetic particles may be difficult in liquid. In addition, pipetting is operable in an open system, so that contamination can more likely take place. When the liquid is packed-and-sealed inside the container as the tube device disclosed in Patent Document 2, Patent Document 3, such pipetting manipulation is not feasible.

Patent Document discloses the method to disperse the magnetic particles in the packed-and-sealed liquid between gelled media, in which the magnetic particles are dispersed in the liquid by blocking or diminishing the magnetic field, and the method to mix and stir the magnetic particles in the liquid while shifting the magnetic particles by an oscillating movement such as amplitude shifting or rotation of magnetic field. Patent Document discloses the method to rotate the device (container) using a rotator as the method of dispersing magnetic particles in liquid.

The above methods cannot disperse, however, satisfactorily magnetic particles and consequently, the yield of the target substance decreases or the degree of examination accuracy is lowered. In addition, relative to such tube devices, the gel adhered to the surface of the magnetic particles causes each other's aggregation of magnetic particles and consequently, dispersion of the magnetic particles may be much harder in liquid. Under consideration of the above state, the purpose of the present invention is to provide a manipulation method of particles to enhance dispersibility of magnetic particles when chemical manipulation using magnetic particles is being performed.

Means for Solving the Problem

According to the study by the inventor, the methods, including blocking magnetic field, annihilation of magnetic field, amplitude shift of the magnetic field, and rotation of the container, allow magnetic particles to move just around the proximity of the inside wall surface of the container and supposedly, dispersion of the particles in the entire liquid is too hard. According to the method of the present invention, dispersibility of particles in liquid can be enhanced by repetition of the movement along the inside wall of the container in the circumferential direction and the movement in the radial direction of the container.

The present invention relates to a method to disperse magnetic particles in liquid filling up a tube container. According to the method of present invention, a step of moving particles along an inside wall of a container in a circumferential direction (circumferential direction movement step); and a step of moving the particles in a radian direction of the container; are repeatedly performed. When the magnetic particles are moved in the circumferential direction, it is preferable that the particles disperse as a band along the inside wall of the container. For example, the particles can be dispersed as the band by increasing the rotation velocity of the container.

The liquid can be packed-and-sealed in the container. Particles are the magnetic particles capable of fixing selectively a specific substance. The specific substance may include nucleic acids, proteins, saccharides, lipids, antibodies, ligands and cells and so forth.

According to an aspect of the present invention, the particle manipulation is performed in the state in which the tube container is placed as the longitudinal direction thereof is horizontal. According to such aspect, when the container rotates, the particles move in the circumferential direction. When rotation of the container slows down or suspends, the particles move as if across the radial direction of the container in the radial direction due to the gravity (gravity of Earth). Then after, when the rotation is accelerated or restarts, the particles move again in the circumferential direction. Movement of particles in the circumferential direction and the radial direction can be repeated also by the reverse rotation of the container in the opposite direction.

According to an aspect of the present invention, particle manipulation is performed by magnetic field manipulation. For example, when the magnetic field varies along the circumferential direction of the container, the particles move in the circumferential direction. When variation of the magnetic field suspends or slows down in the circumferential direction, the particles move along the variation of the magnetic field and as if across the radial direction of the container in the radial direction. The particles also can be moved by changing the intensity of magnetic field from the outside wall of the container. Under the condition in which the container is rotating, the movement of the magnetic particles in the circumferential direction and in the radial direction can repeatedly implemented by changing the magnitude of the magnetic field from the outside wall of the container.

The magnetic particles can be moved from other medium (first medium) to the liquid by the magnetic field manipulation in the longitudinal direction of the container prior to the above particle manipulation. The magnetic particles can be moved from the liquid to other medium (second medium) to the liquid by the magnetic field manipulation in the longitudinal direction of the container following the above particle manipulation. The above "other media" are e.g. liquid and it is preferable that liquid layers are partitioned by such as gelled medium in between.

Further, the present invention relates to a particle manipulation device to perform the above particle manipulation. The particle manipulation device comprises a container holding element to hold the container filled-up with liquid and magnetic particles. The container holding element can be interlocked with a rotation mechanism to rotate the container. The particle manipulation device can comprise a magnetic field applying changeable the magnetic field along the longitudinal direction of the container. The particle manipulation to disperse particles in liquid can be carried out applying the magnetic field due from the magnetic field applying.

Effect of the Invention

According to the method of the present invention, the movement of the magnet in the circumferential direction and the movement thereof in the radial direction are repeatedly taking place, so that the particles can be dispersed in the entire of liquid and the dispersion efficiency of the particles can be improved. Therefore, it can be expected that an efficiency of chemical manipulation, chemical yield and the examination testing system and so forth can be improved In addition, the method according to the present invention is based on a simple manipulation, so that an automation can be easily accomplished.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

Figure 1A:
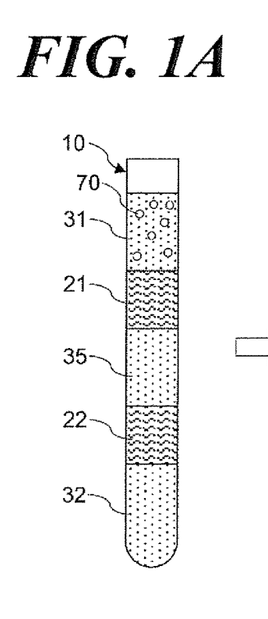
FIG. 1A-FIG. 1C are schematic views illustrating structural aspects of a device by which a manipulation for magnetic particles is performed and a process using the device.
Figure 1B:
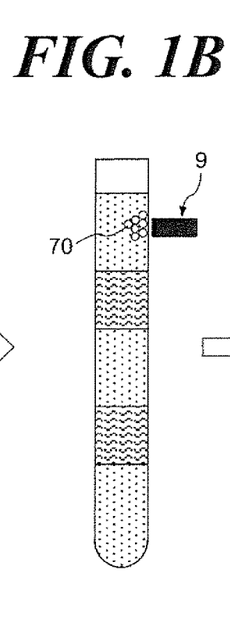
Figure 1C:
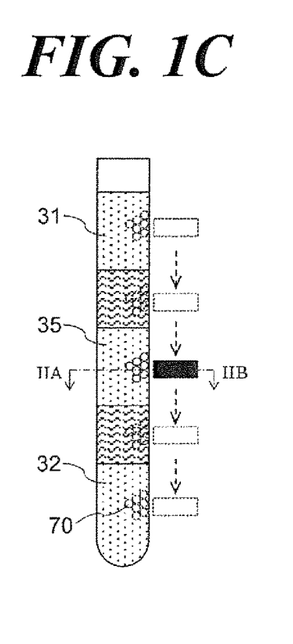

FIG. 1A-FIG. 1C are schematic cross-section views illustrating the (particle manipulation) device applied to the particle manipulation according to the aspect of the present invention. Referring to FIG. 1A, the particle manipulation device comprises a tube container 10 in which liquid layers 32, 35, 31 and the gelled medium layers 22, 21 are alternately layered from the bottom of the container. The gelled medium layer is not miscible in the liquid of the liquid layer adjacent thereto, and insoluble or poorly soluble in such liquids.

Referring to FIG. 1A, the liquid layer 31 at the upper part of the container includes a number of magnetic particles 70. The magnetic particle 70 are capable of specifically fixing a target substance such as a nucleic acid and an antigen and so forth. The target substance in the liquid layer 31 is selectively fixed by dispersing the magnetic particle 70 in the liquid layer 31.

The fixing method capable of fixing the target substance to the magnetic particle is not particularly limited and a variety of fixing mechanisms including known physical adhesion, chemical adhesion and so forth can be applied. For example, a variety of interactions including Van der Waals force, hydrogen bonding, hydrophobic interaction, ion-ion interaction, π-π stacking and so forth can fix the target substance on the surface of the particle or inside thereof.

A particle diameter of the magnetic particle is preferably shorter than 1 mm and further preferably is in the range of 0.1 μm-500 μm. The shape of the particles is preferably a homogeneous spherical shape but can be irregular shape and the distribution of the particle diameter can be in some extent as long as the particle manipulation is operable. The composition unit of the particles can be single substance or can comprise a plurality of substances.

The magnetic particles can be made of just a magnetic material per se, but it is preferable that the magnetic material of which surface is treated with a coating capable of specifically fixing the target substance can be preferably applied. Such magnetic material may include such as iron, cobalt, nickel and so forth and a compound thereof, an oxide thereof and an alloy metal thereof and so forth. Specifically, such magnet can include magnetite ($Fe_3O_4$), hematite ($Fe_2O_3$ or $\alpha Fe_2O_3$), maghemite ($\gamma Fe_2O_3$), titanomagnetite ($xFe_2TiO_4 \cdot (1-x)Fe_3O_4$, ilmenohematite ($xFeTiO_3 \cdot (1-x)Fe_2O_3$, pyrotite ($Fe_{1-x}S(x=0\sim0.13)\square Fe_7S_8(x\sim0.13)$), greigite($Fe_3S_4$), geothite ($\alpha FeOOH$).chromium oxide ($CrO_2$), permalloy, alnico magnet, stainless steel, samarium magnet, neodymium magnet, and barium magnet.

The target substance that can be selectively fixed to the magnetic particles may include biological substances e.g., nucleic acids, proteins, saccharides, lipids, antibodies, ligands and cells per se and so forth. If the target substance is a biological substance, such target substance can be fixed both inside of the particle and on the particle surface by molecular recognition. For example, when the target substance is a nucleic acid, magnetic particles 70 and so forth silica-coated thereon can be preferably applied Further, if the target substance is an antibody (e.g., labeled antibody), a receptor, an antigen and a ligand and so forth, such target substance can be selectively fixed on the particle surface by an amino acid group, a carboxyl group, an epoxy group, apidine, piotine, digoxigenin, protein A, ptotein G and so forth on the particle surface. Such magnetic particles that can fix selectively the specific target substance can be a commercially available product, e.g., Dynabeads® from Life Technologies and MagExtractor® from Toyobo, and so forth.

Referring to FIG. 1B, when the magnet 9 is brought near by the outside wall of the container 10, the magnetic particles fixing the target substances gathers to the inside wall of the container and of the periphery of the magnet 9 due to the action of the magnetic field. Referring to FIG. 1C, when the magnet 9 is moved in the longitudinal direction of the container 10 along the outside wall, the magnetic particles 70 also move in the longitudinal direction of the container 10 following a change of magnetic field, and continuously move to a gelled medium layer 21, a liquid layer 35, a gelled medium layer 22, a liquid layer 32. The most liquid adhering physically to the surrounding of the magnetic particles 70 as a liquid droplet detach from the particle surface when the particles move into the inside of the gelled medium. Although the gelled medium can be perforated by that the entering and movement of particles 71 into the gelled medium layer 21,22 or move, the hole of the gelled medium can be closed by the self-repair action due to the self-restoring ability of the gel. Consequently, almost no liquid flow into the gelled medium through the penetration hole due to the particle.

Manipulations including fixing the target substance to the magnetic particles, washing out foreign materials adhered to the magnetic particle surface, reacting the target substance fixed to the magnetic particles, eluting the target substance fixed to the magnetic particles into the liquid are implemented by dispersing the magnetic particles 70 inside the liquid layer 35 and inside the liquid layer 31 and contacting the magnetic particles to liquid inside the liquid layer. For example, given the substance selectively fixed to the magnetic particles is an antigen, the antigen included inside the liquid layer 31, which is the first medium layer, can be fixed to the magnetic particles 70 coated with molecules capable of selectively fixing antigens such as protein G and protein A and so forth; washing-out to remove foreign materials adhered to the particle surface by dispersing the magnetic particles inside liquid layer 35 can be carried out; an antigen-antibody reaction between the antigen fixed to the particle surface and the antibody inside the liquid layer 32 can be carried out by dispersing the magnetic particles inside liquid layer 32, which is the second medium layer; and a freed-elution of the target substance into the liquid layer 32 can be implemented.

[Dispersion Method of Particles in Liquid]

An aspect of the present invention relates to a particle manipulation method to disperse magnetic particles in a liquid layer. The particle manipulation according to the aspect of the present invention, the movement along the inside wall of the container (movement in the circumferential direction) and the movement crossing the container (movement in the radial direction) are repeatedly implemented. The movement along the inside wall of the container can be implemented by the method including e.g., rotating the container (rotation on the longitudinal axis of the container as the center thereof) and movement of the magnet along the circumferential direction of the container and so forth.

Figure 2A:
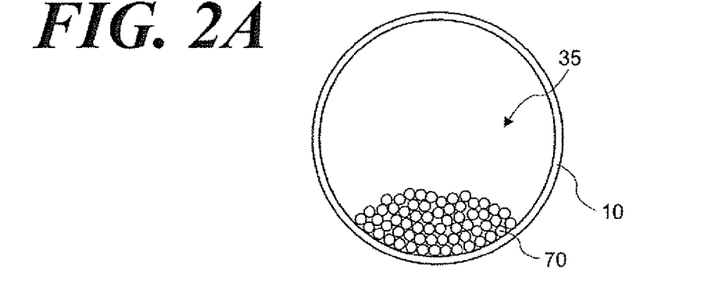
FIG. 2A-FIG. 2D are schematic diagrams illustrating movements of magnetic particles inside a container.

FIG. 2A-FIG. 2D are cross section views of the orthogonal plane (at the line from IIA to IIB in FIG. 1) to the longitudinal direction of the container 10, and schematically illustrating an aspect of the particle movement when the particle manipulation of the present invention is implemented by rotating the container in the state in which the longitudinal direction of the tube (container) is horizontal. In such FIGs., the perpendicular direction is the direction backward from the plane of the paper. Liquid 35 including the magnetic particles 70 are enclosed inside the container 10. FIG. 2A is illustrating the state in which the container is standing while the longitudinal direction thereof is being held to be horizontal and the magnetic particles 70 sediment vertically and downwardly on the inside wall of the container 10 due to the gravity.

Figure 2B:
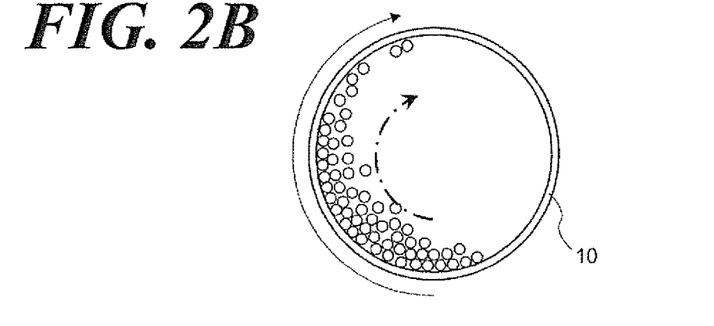
Figure 2C:
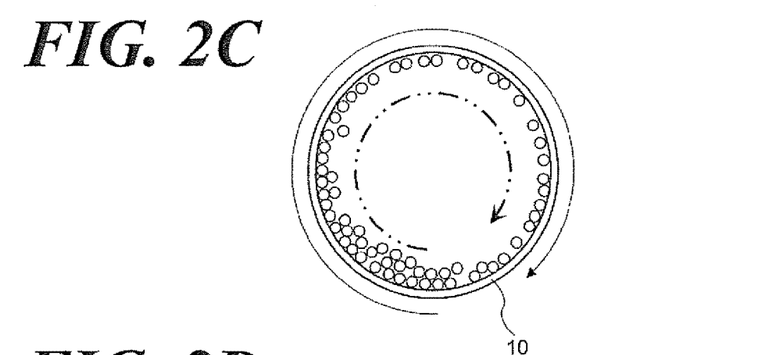

When the container 10 rotates, the magnetic particles in the periphery of the inside wall of the container move along the circumferential direction in the periphery of the inside wall of the container 10 due to actions including wall-friction of liquid in the periphery of the inside wall of the container 10 and the frictional force between the inside wall of the container 10 and the magnetic particles 70 and so forth. Referring to FIG. 2B, a part of particles sustains the state in which the particles sediment vertically and downwardly on the inside wall of the container 10 due to the action of the gravity. When the rotation speed of the container 10 increases, the particles that have been sedimented vertically and downwardly in the container 10 move seriatim along the circumferential direction of the container 10 due to the frictional force between the particles 70 and the inside wall of the container 10, and so forth. Referring to FIG. 2C, when the rotation of the container 10 continues, the particles move along the inside wall of the container 10 in the circumferential direction keeping the state in which the particles 70 are being dispersed as a band over the entire circumference of the inside wall of the container 10.

Figure 2D:
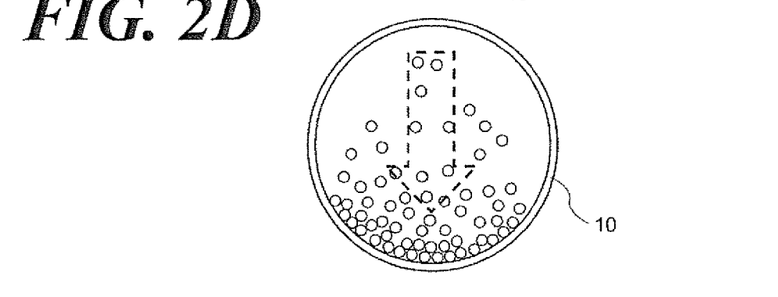

Accordingly, when the magnetic particles are moving along the circumferential direction, the rotation of the container 10 decelerates and suspends, the outside force (e.g., frictional force between the inside wall of the container 10 and liquid and particles) that moves particles in the circumferential direction is weakened. Accordingly, the particles move vertically and downwardly due to the gravity. Referring to FIG. 2D, at this point, the particles 70 move vertically and downwardly inside the liquid layer 35 as crossing the container in the radial direction of the container 10. In addition, "movement in the radial direction" means not only passing the center of the circle, but also includes the movement in the inner side than the inside wall of the container as the movement along the arc chord. Referring to FIG. 2A, when the rotation completely stops, the particles 70 that move in the radial direction of the container sediment on the inside wall of the container 10.

Referring to FIG. 2C again, when the rotation of the container 10 restarts (or accelerates), the particles move in the circumferential direction and become band-like mist (floating objects) along the inside wall of the container and subsequently, are dispersed in the liquid. When the rotation of the container suspends and decelerates, the particles move in the radial direction again as set forth before referring to FIG. 2D.

The movement in the circumferential direction can be implemented continuously without interruption due to thickness of the layer and the volume thereof, so that the particles can be dispersed efficiently like a band compared to the piston movement along the longitudinal direction of the container (tube). Nevertheless, referring to FIG. 2C, given the movement of particles is only in the circumferential direction, dispersion of the particles is limited in the periphery of the inside wall of the liquid layer. According to the particle manipulation of the present invention, the movement in the radial direction following the movement in the circumferential direction is implemented, so that the particle can be dispersed utilizing the entire of the liquid layer 35. In addition, the drag due to liquid is big for the movement in the radial direction, aggregation of particles forming an agglomerate can be easily dispersed. In addition, the movement in the circumferential direction and the movement in the radial direction are repeatedly taking place, so that the entire particles can disperse in accordance with the movement in the radial direction and consequently, the dispersion efficiency of the particles in the liquid can be remarkably improved.

Accordingly, the dispersion efficiency of the particles in the liquid is improved, so that a contacting opportunity between the particles and the liquid can be increased. Therefore, an improvement of a yield of the target substance, an improvement of the purity thereof and an improvement of an examination accuracy can be expected. For example, when the target substance of a liquid sample is fixed to the particle surface, if the above particle manipulation is applied, an amount of the fixed target substance to the particle surface increases, an yield improvement relative to a separation and an extraction and a quantitative performance can be expected.

When the magnetic particles to which the target substance is fixed is washed out, if the above particle manipulation is applied, the foreign materials adhered to the particle surface can be efficiently removed and the purity of the target substance and an examination accuracy can be improved because the contact opportunity between the wash-out solution and the particles increase. In addition, when the reaction between the particles fixing the target substance and the liquid is carried out, the reaction efficiency can be improved if the above particle manipulation is applied. When the particles fixing the target substance are eluted, the yield of the target substance can be improved if the above particle manipulation is applied.

Referring to FIG. 2A-2D, the Embodiment in which movement of the particles in the circumferential direction and the movement of the radial direction are repeated by variation of the rotation speed of the container 10 or repeating rotation and suspension is set forth, but the method of the particle manipulation is not limited thereto. For example, when a rotational direction of the container is reversed from the rotation state in which the particles are moving in the circumferential direction along the inside wall of the container by rotating the container in one direction, a flow of the liquid in the periphery of the inside wall of the container changes and subsequently, the particles in the periphery of the inside wall move to near by the center of the container or to the facing inside wall, so that the movement in the radial direction can be implemented. Specifically, it is repeated the rotational direction is reversed following rotation of the container for the predetermined time and the reversed rotational direction is reversed again following continuous rotation for the predetermined time, so that the movement in the circumferential direction and the movement in the radial direction can be repeatedly implemented.

As set forth above, movements of particles in the circumferential direction and the radial direction are repeatedly implemented by changing the rotation speed and the rotational direction of the container, so that the particles can be dispersed in the liquid. The above method has also an advantage relative to facilitating automation of particle manipulation because no other manipulation than rotating the container is required. An automation of particle manipulation can be accomplished using an equipment comprising a container holding element that holds the container filled up with liquid and particles as the longitudinal direction thereof is horizontal and a rotation mechanism structured to allow the container to be rotatable. The rotation mechanism can be structured to rotate the container holding element.

Figure 3A:
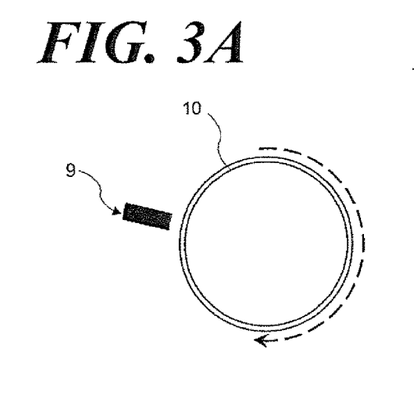
FIG. 3A-FIG. 3C are schematic diagrams illustrating the aspects when the magnetic field varies along the circumferential direction.
Figure 3B:
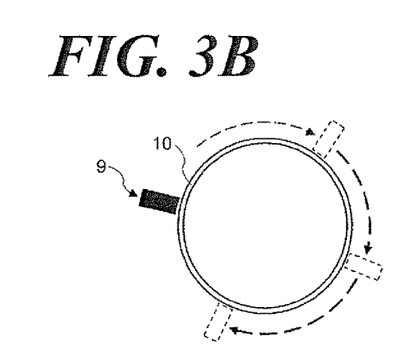
Figure 3C:
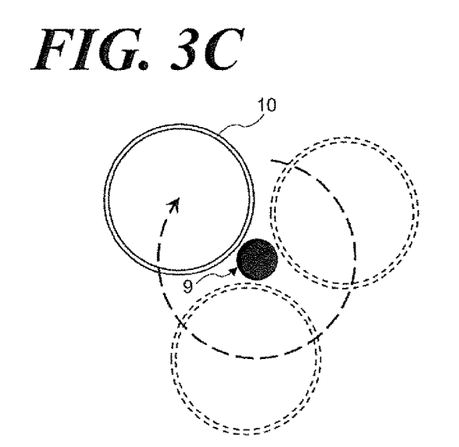

The particles can be moved in the circumferential direction by an external force other than a rotation of the container. Such external force may include an ultrasonic wave of which phase is adjusted to have magnetic force, the gravity and directionality; and a centrifugal force due to the revolution rotation movement of the container. When the magnetic force is applied, referring to FIG. 3A, a method in which a magnet is in-place contacting to the outside (external) wall of the container 10 or in the proximity of the container 10 followed by rotating the container 10, or referring to FIG. 3B, another method in which a magnet is moved along the outside wall of the container 10 or in the proximity of the container 10 followed by moving the magnet 9 in the circumferential direction (i.e., revolving around the axis of the longitudinal direction of the container) and so forth can be included. Referring to FIG. 3C, the change of the magnetic field in the circumferential direction of the container can be also achieved by revolving the container 10 around the magnet 9 as the center thereof.

Figure 3D:
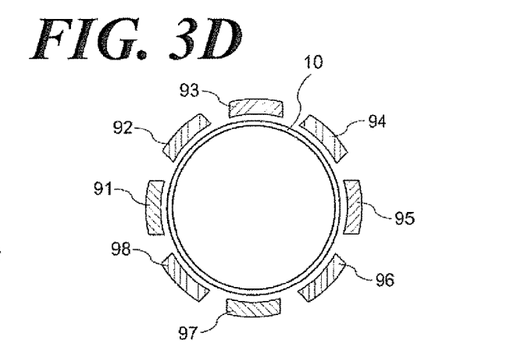
FIG. 3D is a schematic view illustrating a plurality of electric magnets arranged along the circumference of the container.

Instead of permanent magnet, the magnetic field manipulation can be implemented using electric magnets. For example, referring to FIG. 3D, multiple electric magnet 91-98 are in-place around the outer circumference of the container 10 and the magnetic field can be changed in the circumferential direction of the container 10 by changing an electric current of each electric magnet. For example, adjacent electric magnets can be energized by energizing only the electric magnet 91 followed by cutting the electricity to the electric magnet 91 and approximately at the same time energizing the electric magnet 92 and then energizing the adjacent electric magnet seriatim. In addition, the magnetic field in the circumferential direction can be changed by the method of increasing the electricity to the electric magnet 92 while decreasing the electricity to the electric magnet 91 and changing electricity continuously to adjacent electric magnet. The electric current to energize the electric magnet can be alternate current. For example, referring to FIG. 3D, when eight electric magnets 91-98 are in-place around the outer circumference of the container 10 in the equal distance, the magnetic field can be continuously changed in the circumferential direction of the container 10 by delaying alternate phase electric by $\pi/4$ to energize the adjacent electric magnet.

When the magnetic particle manipulation is implemented in accordance with changing magnetic field, an arrangement direction of the container 10 is not restricted and the longitudinal direction of the container 10 can be any direction including the horizontal direction, the vertical direction and the diagonal direction. When the magnetic field is changed in the arrangement state in the horizontal direction or in the diagonal direction, the gravity force in addition to the magnetic force can be available, so that the dispersion efficiency of the particles can be boosted.

When the change of the magnetic field along the circumferential direction is slowed down or suspended under the condition in which the magnetic particles have been moved in the circumferential direction by changing the magnetic field, the external (outside) force that moves the magnetic particles in the circumferential direction is weakened and subsequently, the magnetic particles move in the liquid layer of the container 10 as being pulled by the magnets 91-98. Therefore, the magnetic particles can be moved in the radial direction as well as set forth referring to FIG. 2C, FIG. 2D.

In addition, the magnetic particles also can be moved in the radial direction by changing the intensity of magnetic field from the outside wall of the container 10 under the condition in which the magnetic particles are moved in the circumferential direction by changing the magnetic field. For example, when the container 10 rotates under the condition in which the magnet is distant from the outside wall of the container in the predetermined distance, friction and so forth at the inside wall of the container is more influential than the effect due to the magnetic field, so that the magnetic particles like a band move in the circumferential direction along the inside wall of the container. When the magnet is moved closer to the container 10, the intensity of the magnetic field for the magnetic particles increases, so that the magnetic particles move inside the liquid layer as if being pulled to the magnet.

Figures 4A, 4D:
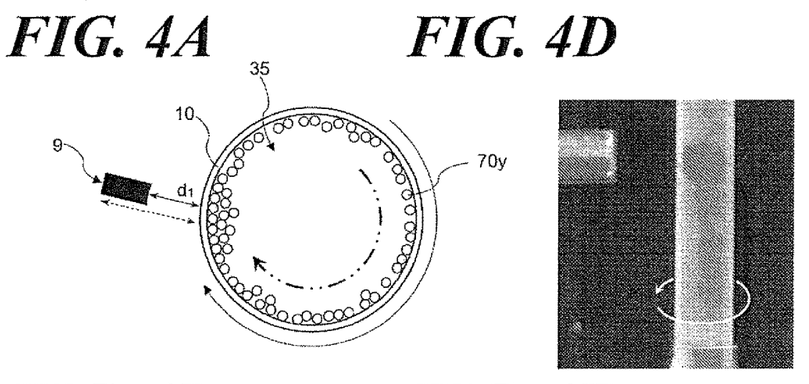
FIG. 4A-FIG. 4C are schematic diagrams illustrating movements of magnetic particles.
FIG. 4D-FIG. 4F are front (observation) photographs of the container corresponding to the respective FIG. 4A, FIG. 4B, and FIG. 4C.
Figures 4B, 4E:
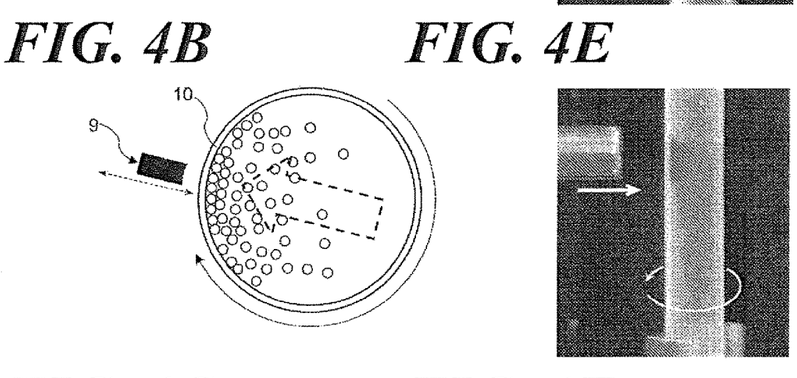
Figures 4C, 4F:
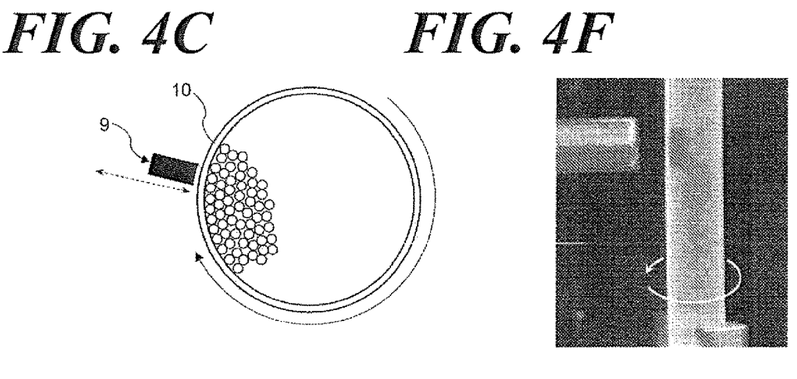

When the particle manipulation is implemented by changing the magnetic field, the movement in the circumferential direction and the movement in the radial direction can be implemented in a series of movements. According to the aspects referring to FIG. 4A-4F, for example, under the condition in which the container is rotating, the step of moving the magnetic particles in the circumferential direction and the step of moving the magnetic particles in the radial direction can be repeatedly implemented by continuously changing the magnitude of the magnetic field from the outside wall of the container. FIG. 4A-FIG. 4C are schematic diagrams illustrating movements of magnetic particles. FIG. 4D-FIG. 4F are front (observation) photographs of the container corresponding to the respective FIG. 4A, FIG. 4B, FIG. 4C.

Referring to FIG. 4A, the container 10 is rotating under the condition in which the magnet 9 is in the distance d 1 from the outside wall of the container 10; the magnetic particles 70y are dispersing like a band along the inside wall of the container and moving in the circumferential direction because the magnetic field added inside the container 10 is small. Referring to FIG. 4B, when the magnet 9 gets closer to the container 10 under the condition in which the container 10 is rotating, the magnetic field added inside the container becomes big, so that the magnetic particles move inside the liquid layer of the container 10 as if being pulled to the magnet 9. Referring to FIG. 4E (photograph), it is understandable that the magnetic particles move as if mists and disperse inside the liquid layer. Referring to FIG. 4C. when the magnet 9 gets much closer to the container 10, the magnetic particles gather in the periphery of the inside wall of the container 10. Referring to FIG. 4A, when the magnet 9 gets away from the container 10, the magnetic particles 70y disperse again like a band along the inside wall of the container 10.

Accordingly, the magnitude of the magnetic field from the outside wall side of the container changes continuously by changing the distance between the container and the magnet while changing the magnetic field along the circumferential direction by keeping the rotation of the container, so that the movement in the circumferential direction and the movement in the radial direction can be repeatedly implemented. In addition, instead of changing the distance between the container 10 and the magnet 9, the electric magnets are in-place in the proximity of the outside wall of the container and the magnitude of the magnetic field from the outside wall of the container can be changed by on-and-off of the electricity to the electric magnets or change of the electricity.

[Structure of the Device]

Referring to FIG. 1, the device in which the gelled medium layer and the liquid layer are layered alternately in the tube container 10 as an example of the device to which the above particle manipulation can be applied is set forth, but the device applicable to the particle manipulation is not particularly limited thereto as long as liquid and magnetic particles are included in the tube container 10.

<Container>

According to the aspect of the present invention, the particle manipulation is implemented in the liquid fill-up in the tube container 10. A material property thereof is not particularly limited as long as being capable of moving the magnetic particles in the container and holding the liquid. It is preferable that the material thereof is magnetically permeable to move the magnetic particles in the container by the magnetic field manipulation from the outside of the container and such materials may include e.g., a polyolefin such as polypropylene, polyethylene and so forth, a fluorine-based resin such as tetrafluoroethylene and so forth, a resin material such as polyvinyl chloride, polystyrene, polycarbonate, cyclic polyolefin and so forth. Other than such materials, ceramic, glass, silicone and nonmagnetic metal and so forth can be applied. Coating with a fluorine-based resin or silicone can be conducted to increase water-repellent property of the inside wall of the container.

Relative to the shape of the container, e.g., a straight-shaped tube having the inner diameter approximately 1-2 mm and the length approximately 50 mm-200 mm can be applied. The tube diameter and the tube length can be appropriately selected depending on an amount of the substance to be processed and an amount of the magnetic particles and so forth. The shape per se thereof is not particularly limited as long as it is a tube-like container. The cross-section shape of the container is preferably a circular shape to facilitate to move the magnetic particles in the circumferential direction, but also can be a oval figure and a polygonal shape. In addition, the container is not required to a straight tube, and the tube may consist of a large diameter part and a small diameter part from the view along the longitudinal direction of the tube.

During or after particle manipulation, if an optical measurement such as absorbance, fluorescence, chemiluminescence, bioluminescence, refractive index variation is conducted or an optical irradiation is conducted, a container having optical transparency can be preferably applied. In addition, if the container is optically transparent, it is preferred because the status of particle manipulation in the container can be visually confirmed. On the other hand, if liquid and magnetic particles must be optically shielded, a container having no optical transparency and blocking light is preferably employed. According to the purpose of use, a container having an optical transparent part and a non-optical transparent part can be employed.

The particle manipulation method according to the aspect of the present invention, a liquid flow obtainable by such as pipetting is not mandatory, so that the manipulation can be implemented in a closed system. If liquid and magnetic particles are filled up and closed, a contamination from outside can be prevented. Accordingly, when the manipulation is implemented while fixing the labile target substance such as RNA, a liquid sensitive (reactive) to such as oxygen in air and so forth, to the magnetic particles, it is particularly advantageous. When the container is subject to a closed system, the opening of the container can be sealed by heating and an appropriate sealing means can be applied to seal. When the particles following manipulation or aqueous liquid following elution of the target substance should be taken out of the container, it is preferred that the opening should be sealed as removable using such as a resin stopper and so forth. In addition, as the device referring to FIG. 1, the liquid can be filled up and sealed by placing the gelled layer and so forth in contact with liquid <Liquid>

[Liquid] Liquid filled-up in the container provides a field for chemical processes including extraction, purification, reaction, separation, detection, analysis and so forth of the target substance fixed on the magnetic particle surface. A type of liquid is not particularly limited, but it is preferred that the liquid does not dissolve the gelled medium when the liquid layers are partitioned by an in-between gelled medium. Accordingly, as such liquid, an aqueous solution including water solution, a mixed solution of water and organic solvent and so forth is preferably applied. Not only liquid is just operative as a medium for chemical processes, but also may be directly involved in such chemical processes or may contain a compound involved in such processes as a component thereof. Such being involved substance in the liquid may include a substance that reacts with a reactive substance fixed to magnetic particles, further reacts with the substance that is fixed on the surface of the magnetic particles by such reaction, a reaction reagent, fluorescent substance, a variety of buffers, surfactants, salts and a variety of other adjutants, and an organic solvent such as alcohol. An aqueous solution can be provided in any forms such as water, water solution and water suspension.

When the target substance included in the liquid sample is fixed on the magnetic particle surface, a variety of foreign materials other than the target substance subjected to be fixed on the magnetic particle surface may be included in the liquid. The liquid sample may include, for example, biological samples; such as animal tissues, plant tissues, body fluid, egesta and so forth; and cells, protozoa, fungi and viruses and so forth which contain nucleic acids. Body fluid includes blood, spinal fluid, saliva, milk and so forth and egesta includes feces, urine, sweat and so forth. Cells may include white blood cells and blood disks in blood, denuded cell of mucosa cells of buccal cells and so forth and white blood cells in saliva and so forth.

The liquid sample containing the target substances such as nucleic acids, antigens and antibodies and so forth can be prepared, for example, in the aspect of a cell suspension solution, a homogenate and a mixed solution with cell lysis solution, and so forth. When the target substance included in the biological samples including blood and so forth is fixed on the particle surface, such liquid sample is a mixture of the biological sample such as blood and so forth and cell lysis solution (nucleic acid extraction solution) from which the target substance is extracted. Such cell lysis solution includes chaotropic substances and surfactants and so forth capable of lysing cells.

<Gelled Medium>

When the liquid layers are partitioned by a in-between gelled medium, the gelled medium can be a gel form or a paste form prior to the particle manipulation. The gelled medium is preferably insoluble or poorly soluble in the adjacent liquid layers and a chemically inert substance. A material or a composition of the gelled medium is not particularly limited. For example, as disclosed in Patent Document WO2012/08624, heating insoluble or poorly soluble liquid substance in water is heated, adding the gelling agent to the heated liquid substance and then dissolving completely the gelling agent followed by cooling to lower temperature than sol-gel transition temperature can form a physical gel.

A chemical gel can be applied to the gelled medium. Such chemical gel may include a hydrocarbon gel such as polyethylene, polypropylene, polyvinyl chloride, (meth)acrylic polymer and so forth; a silicone gel such as polysiloxane, PDMS, silicone hydrogel and so forth; a fluoride gel such as PTFE, PFA, FEP, ETFE, PCTFE and so forth; and a gel or paste mixture including the above gel as a main component; and so forth.

A specific example of the above hydrocarbon gel is a polyehylene Plastibase® including polyethylene as the main component and so forth.

Chemical gel is the composition bridged by covalently binding multiple polymer chains using a chemical reaction and such gelled state is maintained as long as such bridged structure is sustained. Accordingly, the gelled state can be maintained even after passing of the magnetic particles through the gelled medium. When the particle passes through the chemical gelled medium, the gel is perforated temporarily, but the gel is immediately restored by filing in the short-hole with a memory of the gel per se. Therefore, almost no component that originates from the gel per se comes out from the gel, as a foreign material while adhering to the magnetic particle. Accordingly, when such chemical gel is applied to the gelled medium, purification level and detection accuracy of the target substance due to the particle manipulation can be boosted. In addition, when the chemical gel is applied, the fill-up operation of the gel into the container can be easily implemented because no gelation is required inside the container. Such chemical gel is highly stable, so that solation takes place hardly even by physical actions such as transportation period of and vibration during storing the device filled up with the gel and so forth, or even by heating on exposure to a high temperature environment. Accordingly, even when the device is provided under the condition in which the liquid layer and the gelled medium are filled up in the container in advance, stability of device during transportation and storing can be highly ensured.

A silicone gel among the above gels can be preferably applied. A polymer forming the silicone gel is a cross-linked organopolysiloxane selected from the group consisting of cross-linked organopolysiloxane, alkyl-modified partially cross-linked organopolysiloxane, branched silicone alkyl-modified partially crosslinked organopolysiloxane and so forth. Organopolysiloxane may include dimethicone, vinyldimethicone, methyl trimethicone, lauryl dimethicone and co-polymers thereof.

The molecular structure of such polymer is not particularly, limited and may include straight chain, branched chain, cyclic and braided polymers. A silicone gel can be obtained by swelling a polymer (or orgomer) of the above cross-linked organopolysiloxane in oil. The oil that can swell the above polymer and is not misible in water can be preferably applied. Such oil may include cyclopenta siloxane, cyclomethicone, dimethicone, dimethiconol, methyltrimethicone, phenyltrimethicone, diphenylsiloxyphenyltrimethicone, mineral oil, isododecane, isododecyl neopentanoate, trioctanoin, squalane and so forth. For example, gelled or paste siloconce gel can be obtained by mixing the microparticulated crossl-inked organopolysiloxane polymer and the oil.

The silicone gel that is the cross-linked organopolysiloxane swelled with the oil is viscous despite chemical gels having cross-link structure. Consequently, the silicone gel can pass through the magnetic particles and magnetic solid easily, and even if the gel is temporarily perforated, the gel can be restored, so that such gel is suitable for a gelled medium that partitions liquid layers relative to a manipulation using magnetic particles.

Filling gelled medium and liquid in the container can be conducted by an arbitrarily method. When a tube type container is employed, one opened end of the container is sealed prior to filling and preferable gelled medium or liquid are filled through the other opened end in order.

The amount of the gelled medium and liquid to be filled in the container can be determined arbitrarily based on the amount of magnetic particles subject to the manipulation and the type of the manipulation and so forth. If a plurality of gelled medium layers or liquid layers are set, the amount of each layer can be the same or different. A thickness of each layer can be arbitrarily set up. The layer thickness is preferably in the range of e.g., approximately 2 mm-20 mm considering the manipulation thereof and so forth.

[Example of a Particle Manipulation]

As set forth above, according to the manipulation using magnetic particles, separation, purification, reactions, detection and so forth of the target substance are implemented by repeating dispersion of the magnetic particles in liquid and movement of the magnetic particles into the other liquid. For example, when ELISA (Enzyme-linked immuno-sorbent assay) is performed, a reaction of a primary antibody fixed to the magnetic particles and a test antigen is performed in a first liquid including the test antigen (substance to be tested) using the magnetic particles to which the primary antibody is fixed. Accordingly, the test antigen in the liquid is selectively fixed to the magnetic particle surface. An antigen-antibody reaction between an enzyme labeled secondary antibody and the test antigen fixed on the magnetic particle surface is performed in a third liquid following washing out the magnetic particles in a second liquid. Consequently, the secondary antibody is fixed to the magnetic particle surface via the primary antibody and the test antigen. A color reaction is performed between the enzyme binding to the secondary antibody fixed to the particle surface and a coloring agent in a fifth liquid for a predetermined period following washing-out of the magnetic particles in a fourth liquid. A quantitative evaluation can be performed by monitoring such color relation by an absorbance determination using a spectrophotometer. In addition, a qualitative evaluation can be performed by confirming the color reaction by eyes.

The magnetic particles can be moved from the fifth liquid to a sixth liquid following the color reaction in the fifth liquid for a constant time. The color reaction can be suspended by moving the magnetic particles to the outside of the fifth liquid. Accordingly, the qualitative evaluation is feasible without suspending the color reaction by newly adding a reaction suspension reagent such as sodium hydroxide, so that the quantitative measurement is feasible even when the fifth liquid is sealed.

As set forth above, when ELISA is performed, the magnetic particles are moved seriatim and the magnetic particles are dispersed in each liquid to repeat the reaction and washing. Dispersion of particles in each liquid can be implemented using the method according to the aspect of the present invention. A means to transport the particles to the other liquid following dispersion may include the method by which the liquid in the container is removed under the condition in which the particles are gathered in the periphery of the inside wall of the container by bringing the magnet closer to the container and then injected into the other liquid. In addition, referring to FIG. 1, when the device in which the gelled medium layer and the liquid layer are alternately layered in the tube container is applied, the particles passes through the gelled medium layer to move into the other liquid layer by moving the magnet along with the outside wall of the container in the longitudinal direction under the condition in which the particles are gathered in the periphery of the inside wall of the container by bringing the magnet closer to the outside wall of the container.

Figure 5:
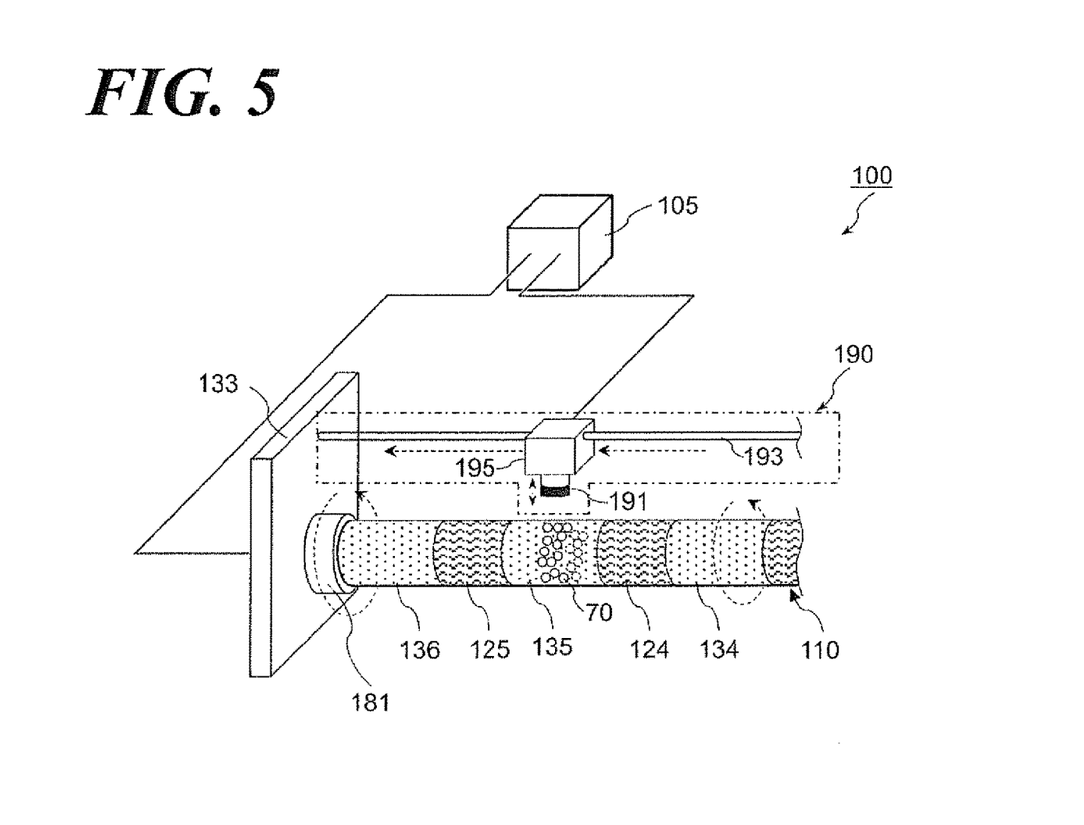
FIG. 5 is a schematic perspective view illustrating a particle manipulation device according to an aspect of the Embodiment.

FIG. 5 is a schematic perspective view illustrating a particle manipulation device feasible for automation according to an aspect of the Embodiment. The apparatus 100 comprises a container holding element 181 installed rotatably to the support board 133. The container holding element 181 can hold the tube container 110 filled up with liquid layers 134, 135, 136 and the gelled media 124, 125 alternately. The holding method of the container 110 is not particularly limited, but preferably the container is held attachably and detachably.

The container holding element 181 connects arbitrarily a driving means such as a motor and so forth, and can change the rotation direction and the rotation speed based on the signal from a control element 105. The container 110 rotates around the axis of the longitudinal direction due to the rotation of the container holding element 181. The magnetic particles 70 in the liquid layer 135 repeats the movement in the circumferential direction and the movement in the radial direction and consequently, disperses in the liquid, by starting and suspending the rotation of the container 110 held by the container holding element 181, changing the rotation speed in high-and-low, and reversing the rotation direction and so forth.

The apparatus 100 further comprises a magnetic field applying element 190. The magnetic field applying element 190 can vary an applying magnetic field. According to the aspect referring to FIG. 5, the magnetic field applying element 190 comprises a guide bar 193 fixed to the supporting board 133 and a magnetic field control mechanism 195 installed slidably to over the guide bar 193. A permanent magnet 191 is mounted to the magnetic field control mechanism 195. The magnetic field control mechanism 195 comprises an arbitrary driving means such as a stepping motor and so forth and can change the position thereof by sliding on the guide bar 193 installed in parallel in the longitudinal direction of the container 110 based on the signal from the control element 105. Accordingly, the magnet 191 is movable along the longitudinal direction of the container and the magnetic field is variable along the longitudinal direction of the container 110. In addition, the magnet 191 mounted to the magnetic field control mechanism 195 can vary the distance from the container 110 based on the signal from the control element 105 Accordingly, the intensity of magnetic field from the outside wall of the container 110 can be varied.

When the particles 70 are dispersed in the liquid layer 135 due to the rotation of the container holding element 181, if the distance between the magnet 191 and the container 110 is set as long, the effect of the magnet field applied to the liquid layer 135 is small, so that the movement of the magnetic particles 70 in the circumferential direction can be implemented smoothly. In addition, when the particles 70 are dispersed in the liquid layer, if the intensity of the magnetic field from the outside wall of the container 110 is varied continuously by moving the magnet 191 mounted to the magnetic field control mechanism 195 up-and-down on the plane of FIG., the magnetic particles 70 can be also dispersed due to the same mechanism as illustrated referring to FIG. 4.

After the magnetic particles 70 are being dispersed in the liquid for the predetermined period, when the rotation of the container holding element 181 is suspended and the magnet 191 is brought closer to the container 110, the magnetic particles 70 are pulled to the magnet 191 and gathered in the periphery of the inside wall of the container 110. Under the above state, the magnetic particles 70 pulled to the magnet 191 move from the liquid layer 135 to the liquid layer 136 via the gelled medium 125 by moving the magnetic field control mechanism 195 along the guide bar 193.

The magnetic particles 70 gathered in the periphery of the inside wall of the container 110 are released from the magnet force and become dispersible in the liquid layer 136 by taking away the magnet 191 from the container 110 following moving the magnetic particles 70 into the liquid layer 136. Under the above state, the magnetic particles 70 in the liquid layer 136 can be dispersed by rotating the container holding element 181 again and controlling the rotation speed and the rotation direction thereof.

Accordingly, when the particle manipulation of the present invention is applied, an automation of the particle dispersion in liquid and the particle movement between liquid layers can be accomplished. In addition, referring to FIG. 5, the inventor sets forth the Embodiment using the permanent magnet 191, but if the electric magnets instead of the permanent magnet are applied, the control of the applied magnetic field can be implemented more easily and accurately.

According to the aspect of the Embodiment referring to FIG. 5, the inventor set forth the Embodiment in which the container 110 rotates by rotating the container holding element 181, but when magnetic particles move in the circumferential direction by the variation of the magnetic field along the circumferential direction of the container 110, the particle manipulation device 100 can be designed as the magnet rotates around the container by revolving the guide bar around the container 110. In addition, the apparatus may implement both rotation and revolving of the container 110.

The inventor set forth ELISA as an example of the manipulation using the magnetic particles, but the aspect of the present invention is applicable to a variety of chemical manipulation using the magnetic particles. For example, when the separation and extraction of nucleic acids using the magnetic particles coated with silica coating are performed, the magnetic particles are dispersed in the sample solution including nucleic acids and after the nucleic acids are fixed to the particle surface, the magnetic particles are moved into the washing solution. After the magnetic particles are dispersed in the washing solution to remove foreign proteins adhered on the surface, the magnetic particles are moved into the nucleic acid elution solution. The magnetic particles are dispersed in the nucleic acid extraction solution, so that the nucleic acids fixed on the particle surface can be recovered.

A cell lysis solution (nucleic acid extraction solution) that is used to extract nucleic acids may include a buffer solution containing a chaotropic substance, a chelating agent such as EDTA and so forth, and tris-hydrogen chloride and so forth. In addition, the cell lysis solution may include a surfactant such as Triton X-100 and so forth. The chaotropic substance may include guanidine hydrochloride, guanidine isothianic acid, potassium iodine, urea and so forth. The cell lysis solution, other than the above materials, may include a protease such as protease K, a variety of buffer agents, and other kinds of adjuvants and any organic solvent such as any alcohol.

When cells in a biological sample are lysed using a cell lysis solution including such as a surfactant, a chaotropic salt and so forth, the magnetic particles are more likely to aggregate together because a wide variety of foreign materials other than the nucleic acids as the target substance are included. As set forth above, when the magnetic particles aggregate due to such as foreign (unwanted) proteins, a movement of the magnetic particles in the radial direction by applying the magnetic field from the outside of the container is effective to disperse efficiently the magnetic particles in the liquid.

Any wash solution can be applied as long as the solution can free the components (e.g., proteins, saccharides and so forth) other than nucleic acids included in the sample and the reagents used for processes, e.g., nucleic acid extraction and so forth, into the wash solution while keeping the state in which nucleic acid is fixed to the particle surface. Such wash solutions may include e.g., high concentration aqueous solution of sodium chloride, potassium chloride, ammonium sulfate and so forth, and aqueous alcohol solution of such as ethanol, isopropanol and so forth.

Water or buffer solution containing low concentration salts can be applied as a nucleic acid eluent. Specifically, tris-buffer, phosphate buffer, distilled water and so forth and more commonly used 5-20 mM tris-buffer solution of adjusted pH 7-9 can be applied. The magnetic particles fixing nucleic acids are dispersed in the eluent, so that the nucleic acid can be freed in the nucleic acid eluent and eluted. The nucleic acids recovered can be, if needed, concentrated or dried followed by being subject to an analysis or a reaction and so forth.

REFERENCE OF SIGNS 10, 110 Container
70 Magnetic particles
9 Magnet
91-98 Electric magnets
130 Liquid layer
31, 32, 35, 134, 135, 36 Liquid (layer)
21, 22, 124, 125 Gelled medium (layer)
100 Particle manipulation device
105 Control element
181 Container holding element (Rotation mechanism)
190 Magnetic field applying element
195 Magnetic field control mechanism Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments.

Also, the inventors intend that only those claims which use the words "means for" are intended to be interpreted under 35 USC 112, sixth paragraph. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. A particle manipulation method, that disperses magnetic particles in a liquid, wherein a tube container is filled up with said liquid that includes a specific substance and said magnetic particles capable of fixing selectively said specific substance in a tube container, comprising steps of:
   in a first step, rotating said container about a rotation axis extending through said container in a first direction;
   in a second step, moving said magnetic particles along an inside wall of said container in a circumferential direction in said liquid;
   in a third step, applying a magnetic field from an outside of said container;
   in a fourth step, moving said magnetic particles along said inside wall of said container in a radian direction;
   in a fifth step, changing continuously one of an intensity and a direction of said magnetic field from said outside of said container; and further comprising:
   in a sixth step repeating said first through fifth steps.

2. The particle manipulation method according to claim 1, wherein:
   said container is closed; and
   said liquid completely fills up said container that is closed.

3. The particle manipulation method according to claim 1, wherein:
   said specific substance that said magnetic particles can fix selectively is at least one selected from the group consisting of: nucleic acids, proteins, saccharides, lipids, antibodies, antigens, ligands and cells.

4. The particle manipulation method according to claim 1, wherein:
a longitudinal direction of said container is a horizontal direction, and said first step of rotating is implemented by rotating said container about said rotation axis in said horizontal direction.

5. The particle manipulation method according to claim 4, wherein:
said step of moving in the circumferential direction and said step of moving in the radian direction are repeated by one of a slowing down and a suspending of said rotation, thereby moving said magnetic particles as crossing in the radial direction of said container due to gravity followed by respectively one of an accelerating or a restarting of said rotation.

6. The particle manipulation method according to claim 4, further comprises the steps of:
reversing a rotational direction of said rotation to a second direction whereby said step of moving in the circumferential direction and said step of moving in the radial direction are repeated.

7. The particle manipulation method according to claim 1, wherein:
said step of moving in the circumferential direction is implemented by variation of a magnetic field along the circumferential direction of said container.

8. The particle manipulation method according to claim 7, wherein:
said step of moving in the radial direction is implemented by at least one of a suspending and a slowing down an intensity variation of the magnetic field along said circumferential direction of the container.

9. The particle manipulation method according to claim 1, wherein:
said step of moving in the circumferential direction is implemented as the magnetic particles disperse in a band-like arrangement along the inside wall of the container generally perpendicular to said rotation axis.

10. The particle manipulation method, according to claim 1, further comprising a step of:
moving said magnetic particles between said liquid and another medium by performing the magnetic field manipulation moving along the longitudinal direction of said container at least before and after the magnetic particles are dispersed by the particle manipulation method.

11. The particle manipulation method according to claim 10, wherein:
said other medium is a liquid; and
said other medium and the liquid, in which the particles are dispersed, are partitioned by a gelled medium interspaced therebetween.

* * * * *